US009707005B2

(12) United States Patent
Strobl et al.

(10) Patent No.: US 9,707,005 B2
(45) Date of Patent: Jul. 18, 2017

(54) LOCKOUT MECHANISMS FOR SURGICAL DEVICES

(71) Applicant: Ethicon LLC, Guaynabo, PR (US)

(72) Inventors: Geoffrey S. Strobl, Williamsburg, OH (US); Mark A. Davison, Mason, OH (US); Megan A. Broderick, West Chester, OH (US); Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 486 days.

(21) Appl. No.: 14/180,826

(22) Filed: Feb. 14, 2014

(65) Prior Publication Data
US 2015/0230816 A1 Aug. 20, 2015

(51) Int. Cl.
*A61B 18/14* (2006.01)
*A61B 17/3201* (2006.01)
(Continued)

(52) U.S. Cl.
CPC ...... *A61B 17/3201* (2013.01); *A61B 18/1445* (2013.01); *A61B 18/18* (2013.01);
(Continued)

(58) Field of Classification Search
CPC ............ A61B 17/3201; A61B 18/1445; A61B 2018/1452; A61B 2018/1455;
(Continued)

(56) References Cited

U.S. PATENT DOCUMENTS 3,662,939 A 5/1972 Bryan
4,438,659 A 3/1984 Desplats
(Continued)

FOREIGN PATENT DOCUMENTS

EP 0070230 A1 1/1983
EP 0324638 A1 7/1989
(Continued)

OTHER PUBLICATIONS

International Search Report and Written Opinion for Application No. PCT/US2015/014954, mailed Jul. 22, 2015 (12 pages).

*Primary Examiner* — Jocelyn D Ram
*Assistant Examiner* — Eunhwa Kim
(74) *Attorney, Agent, or Firm* — Mintz Levin Cohn Ferris Glovsky and Popeo, P.C.

(57) ABSTRACT

Various surgical devices are provided having mechanisms for preventing premature actuation of a cutting mechanism. These devices generally include a handle having one or more actuators and an effector disposed at a distal end of the device and configured to grasp tissue. When the end effector is in an open position, a firing actuator can be positioned so that it cannot be actuated by a user. For example, the firing actuator can be obstructed by a shield or arm when the end effector is in the open position. In other embodiments, the firing actuator can be hidden in a recess formed in the closure actuator until the end effector is moved to the closed position. When the end effector is in the closed position, the firing actuator can be engaged to advance a cutting mechanism, thereby cutting the tissue grasped by the end effector.

17 Claims, 8 Drawing Sheets

(51) Int. Cl.
*A61B 18/18* (2006.01)
*A61B 17/29* (2006.01)
*A61B 90/00* (2016.01)

(52) U.S. Cl.
CPC .............. *A61B 2017/2946* (2013.01); *A61B 2018/1452* (2013.01); *A61B 2018/1455* (2013.01); *A61B 2090/034* (2016.02)

(58) Field of Classification Search
CPC . A61B 18/18; A61B 10/06; A61B 2017/1125; A61B 17/1606; A61B 17/22301; A61B 17/28; A61B 17/285; A61B 17/44; A61B 2090/034; A61B 2017/2946
See application file for complete search history.

(56) References Cited

U.S. PATENT DOCUMENTS

| | | |
|---|---|---|
| 4,527,724 A | 7/1985 | Chow et al. |
| 4,776,506 A | 10/1988 | Green |
| 4,784,137 A | 11/1988 | Kulik et al. |
| 4,850,355 A | 7/1989 | Brooks et al. |
| 4,858,608 A | 8/1989 | McQuilkin |
| 4,863,088 A | 9/1989 | Redmond et al. |
| 4,881,545 A | 11/1989 | Isaacs et al. |
| 4,892,244 A | 1/1990 | Fox et al. |
| 4,907,591 A | 3/1990 | Vasconcellos et al. |
| 4,938,408 A | 7/1990 | Bedi et al. |
| 4,955,959 A | 9/1990 | Tompkins et al. |
| 4,957,499 A | 9/1990 | Lipatov et al. |
| 5,031,814 A | 7/1991 | Tompkins et al. |
| 5,049,152 A | 9/1991 | Simon et al. |
| 5,071,052 A | 12/1991 | Rodak et al. |
| 5,083,695 A | 1/1992 | Foslien et al. |
| 5,111,987 A | 5/1992 | Moeinzadeh et al. |
| 5,129,570 A | 7/1992 | Schulze et al. |
| 5,156,315 A | 10/1992 | Green et al. |
| 5,156,609 A | 10/1992 | Nakao et al. |
| 5,163,945 A | 11/1992 | Ortiz et al. |
| 5,188,274 A | 2/1993 | Moeinzadeh et al. |
| 5,253,793 A | 10/1993 | Green et al. |
| RE34,519 E | 1/1994 | Fox et al. |
| 5,275,612 A | 1/1994 | Bales, Jr. |
| 5,282,808 A | 2/1994 | Kovac et al. |
| 5,286,255 A | 2/1994 | Weber |
| 5,307,976 A | 5/1994 | Olson et al. |
| 5,332,142 A | 7/1994 | Robinson et al. |
| 5,350,356 A | 9/1994 | Bales et al. |
| 5,355,897 A | 10/1994 | Pietrafitta et al. |
| 5,360,154 A | 11/1994 | Green |
| 5,364,001 A | 11/1994 | Bryan |
| 5,366,133 A | 11/1994 | Geiste |
| 5,376,098 A | 12/1994 | Fontayne et al. |
| 5,397,046 A | 3/1995 | Savage et al. |
| 5,413,267 A | 5/1995 | Solyntjes et al. |
| 5,415,335 A | 5/1995 | Knodell, Jr. |
| 5,439,472 A | 8/1995 | Evans et al. |
| 5,443,197 A | 8/1995 | Malis et al. |
| 5,445,304 A | 8/1995 | Plyley et al. |
| 5,445,644 A | 8/1995 | Pietrafitta et al. |
| 5,447,265 A | 9/1995 | Vidal et al. |
| 5,454,824 A | 10/1995 | Fontayne et al. |
| 5,458,279 A | 10/1995 | Plyley |
| 5,462,215 A | 10/1995 | Viola et al. |
| 5,465,896 A | 11/1995 | Allen et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,485,947 A | 1/1996 | Olson et al. |
| 5,487,499 A | 1/1996 | Sorrentino et al. |
| 5,497,934 A | 3/1996 | Brady et al. |
| 5,503,635 A | 4/1996 | Sauer et al. |
| 5,535,935 A | 7/1996 | Vidal et al. |
| 5,547,117 A | 8/1996 | Hamblin et al. |
| 5,547,474 A | 8/1996 | Kloeckl et al. |
| 5,579,978 A | 12/1996 | Green et al. |
| 5,584,425 A | 12/1996 | Savage et al. |
| 5,588,580 A | 12/1996 | Paul et al. |
| 5,588,581 A | 12/1996 | Conlon et al. |
| 5,597,107 A | 1/1997 | Knodel et al. |
| 5,605,272 A | 2/1997 | Witt et al. |
| 5,630,539 A | 5/1997 | Plyley et al. |
| 5,632,432 A | 5/1997 | Schulze et al. |
| 5,634,584 A | 6/1997 | Okorocha et al. |
| 5,636,779 A | 6/1997 | Palmer |
| 5,645,209 A | 7/1997 | Green et al. |
| 5,653,721 A | 8/1997 | Knodel et al. |
| 5,673,842 A | 10/1997 | Bittner et al. |
| 5,678,748 A | 10/1997 | Plyley et al. |
| 5,680,983 A | 10/1997 | Plyley et al. |
| 5,697,543 A | 12/1997 | Burdorff |
| 5,700,270 A | 12/1997 | Peyser et al. |
| 5,706,998 A | 1/1998 | Plyley et al. |
| 5,709,334 A | 1/1998 | Sorrentino et al. |
| 5,715,988 A | 2/1998 | Palmer |
| 5,718,359 A | 2/1998 | Palmer et al. |
| 5,730,740 A | 3/1998 | Wales et al. |
| 5,735,445 A | 4/1998 | Vidal et al. |
| 5,735,874 A | 4/1998 | Measamer et al. |
| 5,755,726 A | 5/1998 | Pratt et al. |
| 5,758,814 A | 6/1998 | Gallagher et al. |
| 5,762,255 A | 6/1998 | Chrisman et al. |
| 5,782,749 A | 7/1998 | Riza |
| 5,792,149 A | 8/1998 | Sherts et al. |
| 5,799,857 A | 9/1998 | Robertson et al. |
| 5,807,393 A | 9/1998 | Williamson, IV et al. |
| 5,868,784 A | 2/1999 | Riza |
| 5,878,938 A | 3/1999 | Bittner et al. |
| 5,893,506 A | 4/1999 | Powell |
| 5,894,979 A | 4/1999 | Powell |
| 5,895,394 A | 4/1999 | Kienzle et al. |
| 5,918,791 A | 7/1999 | Sorrentino et al. |
| 5,972,000 A | 10/1999 | Beyar et al. |
| 5,988,479 A | 11/1999 | Palmer |
| 6,010,054 A | 1/2000 | Johnson et al. |
| 6,024,741 A | 2/2000 | Williamson, IV et al. |
| 6,045,566 A | 4/2000 | Pagedas |
| 6,066,151 A | 5/2000 | Miyawaki et al. |
| 6,079,606 A | 6/2000 | Milliman et al. |
| 6,083,234 A | 7/2000 | Nicholas et al. |
| 6,109,500 A | 8/2000 | Alli et al. |
| 6,131,789 A | 10/2000 | Schulze et al. |
| 6,155,473 A | 12/2000 | Tompkins et al. |
| 6,257,351 B1 | 7/2001 | Ark et al. |
| 6,440,144 B1 | 8/2002 | Bacher |
| 6,446,854 B1 | 9/2002 | Remiszewski et al. |
| 6,547,798 B1 | 4/2003 | Yoon et al. |
| 6,669,073 B2 | 12/2003 | Milliman et al. |
| 6,695,198 B2 | 2/2004 | Adams et al. |
| 6,773,438 B1 | 8/2004 | Knodel et al. |
| 6,959,852 B2 | 11/2005 | Shelton, IV et al. |
| 6,988,649 B2 | 1/2006 | Shelton, IV et al. |
| 7,044,352 B2 | 5/2006 | Shelton, IV et al. |
| 7,055,730 B2 | 6/2006 | Ehrenfels et al. |
| 7,083,075 B2 | 8/2006 | Swayze et al. |
| 7,097,089 B2 | 8/2006 | Marczyk |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,147,140 B2 | 12/2006 | Wukusick et al. |
| 7,150,749 B2 | 12/2006 | Dycus et al. |
| 7,156,846 B2 | 1/2007 | Dycus et al. |
| 7,207,472 B2 | 4/2007 | Wukusick et al. |
| 7,211,091 B2 | 5/2007 | Fowler et al. |
| 7,225,963 B2 | 6/2007 | Scirica |
| 7,226,408 B2 | 6/2007 | Harai et al. |
| 7,232,440 B2 | 6/2007 | Dumbauld et al. |
| 7,270,439 B2 | 9/2007 | Horrell et al. |
| 7,300,444 B1 | 11/2007 | Nielsen et al. |
| 7,303,107 B2 | 12/2007 | Milliman et al. |

(56) References Cited

U.S. PATENT DOCUMENTS

| | | |
|---|---|---|
| 7,322,994 B2 | 1/2008 | Nicholas et al. |
| 7,328,828 B2 | 2/2008 | Ortiz et al. |
| 7,334,717 B2 | 2/2008 | Rethy et al. |
| 7,341,145 B2 | 3/2008 | Vandenbroek et al. |
| 7,380,695 B2 | 6/2008 | Doll et al. |
| 7,419,080 B2 | 9/2008 | Smith et al. |
| 7,419,495 B2 | 9/2008 | Menn et al. |
| 7,434,715 B2 | 10/2008 | Shelton, IV et al. |
| 7,464,846 B2 | 12/2008 | Shelton, IV et al. |
| 7,472,814 B2 | 1/2009 | Mastri et al. |
| 7,485,124 B2 | 2/2009 | Kuhns et al. |
| 7,487,899 B2 | 2/2009 | Shelton, IV et al. |
| 7,513,408 B2 | 4/2009 | Shelton, IV et al. |
| 7,549,564 B2 | 6/2009 | Boudreaux |
| 7,552,854 B2 | 6/2009 | Wixey et al. |
| 7,556,186 B2 | 7/2009 | Milliman |
| 7,568,604 B2 | 8/2009 | Ehrenfels et al. |
| 7,597,229 B2 | 10/2009 | Boudreaux et al. |
| 7,600,663 B2 | 10/2009 | Green |
| 7,635,385 B2 | 12/2009 | Milliman et al. |
| 7,637,410 B2 | 12/2009 | Marczyk |
| 7,637,917 B2 | 12/2009 | Whitfield et al. |
| 7,641,092 B2 | 1/2010 | Kruszynski et al. |
| 7,641,093 B2 | 1/2010 | Doll et al. |
| 7,694,865 B2 | 4/2010 | Scirica |
| 7,703,653 B2 | 4/2010 | Shah et al. |
| 7,717,931 B2 | 5/2010 | Himes |
| 7,721,931 B2 | 5/2010 | Shelton, IV et al. |
| 7,721,933 B2 | 5/2010 | Ehrenfels et al. |
| 7,721,936 B2 | 5/2010 | Shalton, IV et al. |
| 7,731,073 B2 | 6/2010 | Wixey et al. |
| 7,731,725 B2 | 6/2010 | Gadberry et al. |
| 7,753,246 B2 | 7/2010 | Scirica |
| 7,771,425 B2 | 8/2010 | Dycus et al. |
| 7,789,283 B2 | 9/2010 | Shah |
| 7,819,298 B2 | 10/2010 | Hall et al. |
| 7,819,886 B2 | 10/2010 | Whitfield et al. |
| 7,832,612 B2 | 11/2010 | Baxter, III et al. |
| 7,857,812 B2 | 12/2010 | Dycus et al. |
| 7,886,952 B2 | 2/2011 | Scirica et al. |
| 7,886,953 B2 | 2/2011 | Schwemberger et al. |
| 7,891,532 B2 | 2/2011 | Mastri et al. |
| 7,896,213 B2 | 3/2011 | Hiranuma et al. |
| 7,900,806 B2 | 3/2011 | Chen et al. |
| 7,905,381 B2 | 3/2011 | Baxter, III et al. |
| 7,905,890 B2 | 3/2011 | Whitfield et al. |
| 7,918,230 B2 | 4/2011 | Whitman et al. |
| 7,934,629 B2 | 5/2011 | Wixey et al. |
| 7,942,300 B2 | 5/2011 | Rethy et al. |
| 7,942,303 B2 | 5/2011 | Shah |
| 7,954,684 B2 | 6/2011 | Boudreaux |
| 7,967,180 B2 | 6/2011 | Scirica |
| 7,975,895 B2 | 7/2011 | Milliman |
| 7,992,758 B2 | 8/2011 | Whitman et al. |
| 8,011,554 B2 | 9/2011 | Milliman |
| 8,015,976 B2 | 9/2011 | Shah |
| 8,021,375 B2 | 9/2011 | Aldrich et al. |
| 8,029,477 B2 | 10/2011 | Byrum et al. |
| 8,033,438 B2 | 10/2011 | Scirica |
| 8,066,167 B2 | 11/2011 | Measamer et al. |
| 8,070,033 B2 | 12/2011 | Milliman et al. |
| 8,070,760 B2 | 12/2011 | Fujita |
| 8,074,861 B2 | 12/2011 | Ehrenfels et al. |
| 8,074,862 B2 | 12/2011 | Shah |
| 8,096,459 B2 | 1/2012 | Ortiz et al. |
| 8,128,643 B2 | 3/2012 | Aranyi et al. |
| 8,146,790 B2 | 4/2012 | Milliman |
| 8,147,504 B2 | 4/2012 | Ino et al. |
| 8,157,148 B2 | 4/2012 | Scirica |
| 8,205,619 B2 | 6/2012 | Shah et al. |
| 8,225,979 B2 | 7/2012 | Farascioni et al. |
| 8,267,945 B2 | 9/2012 | Nguyen et al. |
| 8,267,946 B2 | 9/2012 | Whitfield et al. |
| 8,276,594 B2 | 10/2012 | Shah |
| 8,292,158 B2 | 10/2012 | Sapienza |
| 8,308,743 B2 | 11/2012 | Matsuno et al. |
| 8,322,589 B2 | 12/2012 | Boudreaux |
| 8,328,064 B2 | 12/2012 | Racenet et al. |
| 8,333,313 B2 | 12/2012 | Boudreaux et al. |
| 8,336,754 B2 | 12/2012 | Cappola et al. |
| 8,342,377 B2 | 1/2013 | Milliman et al. |
| 8,360,294 B2 | 1/2013 | Scirica |
| 8,360,296 B2 | 1/2013 | Zingman |
| 8,365,974 B2 | 2/2013 | Milliman |
| 8,382,773 B2 | 2/2013 | Whitfield et al. |
| 8,397,972 B2 | 3/2013 | Kostrzewski |
| 8,424,737 B2 | 4/2013 | Scirica |
| 8,465,502 B2 | 6/2013 | Zergiebel |
| 8,496,673 B2 | 7/2013 | Nguyen et al. |
| 8,567,655 B2 | 10/2013 | Nalagatla et al. |
| 8,573,463 B2 | 11/2013 | Scirica et al. |
| 8,579,918 B2 | 11/2013 | Whitfield et al. |
| 8,584,919 B2 | 11/2013 | Hueil et al. |
| 8,590,763 B2 | 11/2013 | Milliman |
| 8,603,109 B2 | 12/2013 | Aranyi et al. |
| 8,608,044 B2 | 12/2013 | Hueil et al. |
| 8,616,428 B2 | 12/2013 | Milliman et al. |
| 8,627,993 B2 | 1/2014 | Smith et al. |
| 8,631,990 B1 | 1/2014 | Park et al. |
| 8,632,535 B2 | 1/2014 | Shelton, IV et al. |
| 8,636,766 B2 | 1/2014 | Milliman et al. |
| 8,652,151 B2 | 2/2014 | Lehman et al. |
| 8,684,248 B2 | 4/2014 | Milliman |
| 8,685,004 B2 | 4/2014 | Zemlock et al. |
| 8,695,866 B2 | 4/2014 | Leimbach et al. |
| 8,701,962 B2 | 4/2014 | Kostrzewski |
| 8,708,210 B2 | 4/2014 | Zemlok et al. |
| 8,708,212 B2 | 4/2014 | Williams |
| 8,721,630 B2 | 5/2014 | Ortiz et al. |
| 8,728,099 B2 | 5/2014 | Cohn et al. |
| 8,728,118 B2 | 5/2014 | Hinman et al. |
| 8,730,053 B2 | 5/2014 | Dycus |
| 8,733,611 B2 | 5/2014 | Milliman |
| 8,740,036 B2 | 6/2014 | Williams |
| 8,740,039 B2 | 6/2014 | Farascioni |
| 8,740,932 B2 | 6/2014 | Whitman et al. |
| 8,746,534 B2 | 6/2014 | Farascioni |
| 8,752,748 B2 | 6/2014 | Whitman et al. |
| 2004/0138681 A1 | 7/2004 | Pier |
| 2004/0167545 A1 | 8/2004 | Sadler et al. |
| 2005/0159752 A1 | 7/2005 | Walker et al. |
| 2006/0009790 A1 | 1/2006 | Blake et al. |
| 2006/0079115 A1 | 4/2006 | Aranyi et al. |
| 2006/0185682 A1 | 8/2006 | Marczyk |
| 2007/0010838 A1 | 1/2007 | Shelton et al. |
| 2007/0027468 A1 | 2/2007 | Wales et al. |
| 2007/0175955 A1 | 8/2007 | Shelton et al. |
| 2007/0282355 A1 | 12/2007 | Brown et al. |
| 2008/0004639 A1 | 1/2008 | Huitema et al. |
| 2008/0061108 A1 | 3/2008 | Scirica |
| 2008/0083807 A1 | 4/2008 | Beardsley et al. |
| 2008/0281336 A1 | 11/2008 | Zergiebel |
| 2009/0048625 A1* | 2/2009 | Pedersen ............ A61B 17/2909 606/205 |
| 2009/0206130 A1 | 8/2009 | Hall et al. |
| 2009/0206131 A1 | 8/2009 | Weisenburgh, II et al. |
| 2010/0059571 A1 | 3/2010 | Chen et al. |
| 2010/0065604 A1 | 3/2010 | Weng |
| 2010/0163598 A1 | 7/2010 | Belzer |
| 2010/0193566 A1 | 8/2010 | Scheib et al. |
| 2010/0256634 A1 | 10/2010 | Voegele et al. |
| 2010/0298849 A1 | 11/2010 | Lazic |
| 2010/0301097 A1 | 12/2010 | Scirica et al. |
| 2010/0318104 A1 | 12/2010 | Lazic |
| 2010/0327041 A1 | 12/2010 | Milliman et al. |
| 2011/0054498 A1 | 3/2011 | Monassevitch et al. |
| 2011/0068148 A1 | 3/2011 | Hall et al. |
| 2011/0155787 A1 | 6/2011 | Baxter, III et al. |
| 2011/0208212 A1 | 8/2011 | Zergiebel et al. |
| 2012/0080475 A1 | 4/2012 | Smith et al. |
| 2012/0179171 A1 | 7/2012 | Cohen et al. |
| 2012/0184990 A1 | 7/2012 | Twomey |
| 2012/0193399 A1 | 8/2012 | Holcomb et al. |
| 2012/0234893 A1 | 9/2012 | Schuckmann et al. |

(56) References Cited

U.S. PATENT DOCUMENTS

| | | |
|---|---|---|
| 2012/0248167 A1 | 10/2012 | Flanagan et al. |
| 2012/0325888 A1 | 12/2012 | Qiao et al. |
| 2013/0015230 A1 | 1/2013 | Wixey et al. |
| 2013/0037594 A1 | 2/2013 | Dhakad et al. |
| 2013/0037597 A1 | 2/2013 | Katre et al. |
| 2013/0068818 A1 | 3/2013 | Kasvikis |
| 2013/0075444 A1 | 3/2013 | Cappola et al. |
| 2013/0105545 A1 | 5/2013 | Burbank |
| 2013/0105551 A1 | 5/2013 | Zingman |
| 2013/0105555 A1 | 5/2013 | Kasvikis |
| 2013/0153630 A1 | 6/2013 | Miller et al. |
| 2013/0153631 A1 | 6/2013 | Vasudevan et al. |
| 2013/0165951 A1* | 6/2013 | Blake, III |
| 2013/0168435 A1 | 7/2013 | Huang et al. |
| 2013/0172887 A1 | 7/2013 | Ichikawa et al. |
| 2013/0175316 A1 | 7/2013 | Thompson et al. |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0184718 A1 | 7/2013 | Smith et al. |
| 2013/0184719 A1 | 7/2013 | Shelton, IV et al. |
| 2013/0186933 A1 | 7/2013 | Shelton, IV et al. |
| 2013/0190732 A1 | 7/2013 | Slisz et al. |
| 2013/0193188 A1 | 8/2013 | Shelton, IV et al. |
| 2013/0200130 A1 | 8/2013 | Wenchell et al. |
| 2013/0206813 A1 | 8/2013 | Nalagatla |
| 2013/0214029 A1 | 8/2013 | Scirica |
| 2013/0221066 A1 | 8/2013 | Scirica et al. |
| 2013/0231643 A1 | 9/2013 | Farascioni et al. |
| 2013/0248577 A1 | 9/2013 | Leimbach et al. |
| 2013/0264370 A1 | 10/2013 | Chen et al. |
| 2013/0264372 A1 | 10/2013 | Chen et al. |
| 2013/0274767 A1 | 10/2013 | Sorrentino et al. |
| 2013/0277410 A1 | 10/2013 | Fernandez et al. |
| 2013/0284789 A1 | 10/2013 | Smith et al. |
| 2013/0306703 A1 | 11/2013 | Ehrenfels et al. |
| 2013/0310850 A1 | 11/2013 | Glick et al. |
| 2013/0310852 A1 | 11/2013 | Bolduc et al. |
| 2013/0327808 A1 | 12/2013 | Chen et al. |
| 2014/0000411 A1 | 1/2014 | Shelton, IV et al. |
| 2014/0001231 A1 | 1/2014 | Shelton, IV et al. |
| 2014/0001232 A1 | 1/2014 | Cappola et al. |
| 2014/0001233 A1 | 1/2014 | Cappola et al. |
| 2014/0001234 A1 | 1/2014 | Shelton, IV et al. |
| 2014/0005695 A1 | 1/2014 | Shelton, IV |
| 2014/0008413 A1 | 1/2014 | Williams |
| 2014/0014706 A1 | 1/2014 | Rajappa et al. |
| 2014/0021239 A1 | 1/2014 | Kostrzewski |
| 2014/0027491 A1 | 1/2014 | Beardsley et al. |
| 2014/0033517 A1 | 2/2014 | Smith |
| 2014/0042206 A1 | 2/2014 | Milliman |
| 2014/0048581 A1 | 2/2014 | Scirica et al. |
| 2014/0058412 A1 | 2/2014 | Aranyi et al. |
| 2014/0061279 A1 | 3/2014 | Laurent et al. |
| 2014/0110453 A1 | 4/2014 | Wingardner et al. |
| 2014/0110454 A1 | 4/2014 | Milliman et al. |
| 2014/0131417 A1 | 5/2014 | Williams |
| 2014/0135832 A1 | 5/2014 | Park et al. |
| 2014/0150600 A1 | 6/2014 | Zemlok et al. |
| 2014/0151430 A1 | 6/2014 | Scheib et al. |
| 2014/0158744 A1 | 6/2014 | Patel et al. |
| 2014/0158745 A1 | 6/2014 | Milliman |
| 2014/0175149 A1 | 6/2014 | Smith et al. |
| 2014/0358142 A1* | 12/2014 | Miller ............... A61B 18/1447 606/47 |

FOREIGN PATENT DOCUMENTS

| | | |
|---|---|---|
| EP | 0332413 A1 | 9/1989 |
| EP | 0336596 A1 | 10/1989 |
| EP | 0489436 A1 | 6/1992 |
| EP | 0491537 A2 | 6/1992 |
| EP | 0509554 A1 | 10/1992 |
| EP | 0510826 | 10/1992 |
| EP | 0512209 A2 | 11/1992 |
| EP | 0537498 A2 | 4/1993 |
| EP | 0541987 A1 | 5/1993 |
| EP | 0545029 A1 | 6/1993 |
| EP | 0552423 A2 | 7/1993 |
| EP | 0555103 A1 | 8/1993 |
| EP | 0566404 A2 | 10/1993 |
| EP | 0579038 A1 | 1/1994 |
| EP | 0621006 A1 | 10/1994 |
| EP | 0630616 A2 | 12/1994 |
| EP | 0634141 A1 | 1/1995 |
| EP | 0643946 A2 | 3/1995 |
| EP | 0646354 A2 | 4/1995 |
| EP | 0656188 A2 | 6/1995 |
| EP | 0656189 A2 | 6/1995 |
| EP | 0677273 A2 | 10/1995 |
| EP | 0695532 A2 | 2/1996 |
| EP | 0696178 A1 | 2/1996 |
| EP | 0717959 A2 | 6/1996 |
| EP | 0724862 A2 | 8/1996 |
| EP | 0749287 A1 | 12/1996 |
| EP | 0754433 A2 | 1/1997 |
| EP | 0769275 A1 | 4/1997 |
| EP | 0793943 A1 | 9/1997 |
| EP | 0795298 A2 | 9/1997 |
| EP | 0795299 A2 | 9/1997 |
| EP | 0813843 A1 | 12/1997 |
| EP | 0875208 A2 | 11/1998 |
| EP | 1175869 A1 | 1/2002 |
| EP | 1199038 A2 | 4/2002 |
| EP | 1300117 A2 | 4/2003 |
| EP | 1319370 A2 | 6/2003 |
| EP | 1354560 A2 | 10/2003 |
| EP | 1405601 A1 | 4/2004 |
| EP | 1479345 A1 | 11/2004 |
| EP | 1479347 | 11/2004 |
| EP | 1479348 | 11/2004 |
| EP | 1523943 A1 | 4/2005 |
| EP | 1523944 A1 | 4/2005 |
| EP | 1550413 A1 | 7/2005 |
| EP | 1552791 A1 | 7/2005 |
| EP | 1563791 A1 | 8/2005 |
| EP | 1563792 A1 | 8/2005 |
| EP | 1563794 A1 | 8/2005 |
| EP | 1520523 | 12/2005 |
| EP | 1611857 A1 | 1/2006 |
| EP | 1621138 A2 | 2/2006 |
| EP | 1621142 A2 | 2/2006 |
| EP | 1621144 A2 | 2/2006 |
| EP | 1690501 A1 | 8/2006 |
| EP | 1690502 A1 | 8/2006 |
| EP | 1733686 A2 | 12/2006 |
| EP | 1749485 A1 | 2/2007 |
| EP | 1749486 A1 | 2/2007 |
| EP | 1754446 A2 | 2/2007 |
| EP | 1757237 A1 | 2/2007 |
| EP | 1762190 A2 | 3/2007 |
| EP | 1774916 A1 | 4/2007 |
| EP | 1782738 A2 | 5/2007 |
| EP | 1813197 A2 | 8/2007 |
| EP | 1813200 A2 | 8/2007 |
| EP | 1813204 A1 | 8/2007 |
| EP | 1854416 A1 | 11/2007 |
| EP | 1857058 A1 | 11/2007 |
| EP | 1908413 A1 | 4/2008 |
| EP | 1964523 A1 | 9/2008 |
| EP | 2090246 A2 | 8/2009 |
| EP | 2455006 A2 | 5/2012 |
| EP | 2 529 681 A1 | 12/2012 |
| JP | 2009291535 A | 12/2009 |
| JP | 2010035820 A | 2/2010 |
| JP | 2013184058 A | 9/2013 |
| WO | 9210976 | 7/1992 |
| WO | 9217120 A2 | 10/1992 |
| WO | 9408525 A1 | 4/1994 |
| WO | 9424943 A1 | 11/1994 |
| WO | 9502366 A1 | 1/1995 |
| WO | 9503741 A2 | 2/1995 |
| WO | 9523557 A1 | 9/1995 |

(56) References Cited

FOREIGN PATENT DOCUMENTS

| | | | |
|---|---|---|---|
| WO | 9529639 | A1 | 11/1995 |
| WO | 9629936 | A1 | 10/1996 |
| WO | 9915086 | A1 | 4/1999 |
| WO | 0182847 | A2 | 11/2001 |
| WO | 0215797 | A1 | 2/2002 |
| WO | 03030743 | A2 | 4/2003 |
| WO | 2004032766 | A2 | 4/2004 |
| WO | 2004052410 | A2 | 6/2004 |
| WO | 2006042076 | A2 | 4/2006 |
| WO | 2006042084 | A2 | 4/2006 |
| WO | 2006042110 | A2 | 4/2006 |
| WO | 2006042141 | A2 | 4/2006 |
| WO | 2007068181 | A1 | 6/2007 |
| WO | 2008075682 | A1 | 6/2008 |
| WO | 2008127968 | A2 | 10/2008 |
| WO | 2010077228 | A1 | 7/2010 |
| WO | 2010090940 | A1 | 8/2010 |
| WO | 2012177409 | A1 | 12/2012 |
| WO | 2013181929 | A1 | 12/2013 |
| WO | 2013181930 | A1 | 12/2013 |
| WO | 2014011257 | A1 | 1/2014 |

\* cited by examiner

LOCKOUT MECHANISMS FOR SURGICAL DEVICES

FIELD

The present invention relates to surgical devices that are configured to prevent premature actuation of a cutting mechanism, and methods of using the same.

BACKGROUND

Various surgical devices utilize a multi-step process to grasp and cut tissue, such as staplers, surgical shears, and RF tissue sealers. In general, these devices have first and second jaws configured to grasp tissue therebetween, and a cutting mechanism configured to sever the tissue that is positioned between the jaws. Certain devices can also include one or more clips or staples for fastening the tissue, and/or electrodes for delivering energy to the tissue. Such devices can have a single actuator for performing a number of functions, but more commonly have a number of independently operable actuators, including a closure actuator for moving the jaws between open and closed positions, and a firing actuator for advancing the cutting mechanism along the jaws to sever the grasped tissue and optionally firing staples and/or delivering RF energy to the tissue.

Where independent actuators are provided, a user will often engage the first actuator to close the jaws and grasp tissue prior to engaging the second actuator to advance the cutting mechanism and/or perform other functions. However, the steps are not always performed in the intended order. During a surgical procedure, it can be difficult for the surgeon to distinguish between the first, closure actuator and the second, cutting actuator. When a surgeon engages the second actuator prior to tissue being positioned between the jaws, this can cause injury in an unintended area of tissue and/or jam the cutting mechanism of the device.

Accordingly, there is a need for a device that is configured to prevent a user from prematurely actuating a cutting mechanism, and methods of using the same.

SUMMARY

Surgical devices having various actuation systems are provided herein. In one embodiment, a surgical device is provided and includes an end effector having first and second jaws configured to move relative to one another between an open position in which the jaws are spaced a distance apart from one another and a closed position in which the jaws are configured to grasp tissue therebetween. The device also includes a handle portion having a first actuator and a second actuator. The first actuator is operatively associated with the first and second jaws and movable between a first position and a second position. Movement of the actuator from the first position to the second position is effective to move the jaws from the open position to the closed position. The second actuator is configured to advance a cutting element distally along the first and second jaws to cut tissue grasped therebetween, the second actuator having an opening configured to receive a user's finger. At least one blocking member can be configured to move relative to the second actuator depending on the position of the first actuator. The device can be configured such that, when the first actuator is in the first position and the jaws are in the open position, the at least one blocking member obstructs the opening of the second actuator so that the second actuator cannot be manually actuated by a user.

The device can have a variety of configurations. In one embodiment, the at least one blocking member includes first and second blocking members, the first blocking member configured to be positioned on a first side of the second actuator and the second blocking member configured to be positioned on a second side of the second actuator. In certain aspects, the at least one blocking member can include a blocking shield configured to substantially cover the opening of the second actuator. In other aspects, the at least one blocking member can include a blocking arm configured to partially cover the opening of the second actuator. In still other aspects, the opening of the second actuator can be configured to be exposed, in response to movement of the first actuator from the first position to the second position, such that the second actuator can be actuated to advance the cutting element. The device can also perform various other functions, such as firing staples and/or delivering energy to tissue engaged between the first and second jaws as the cutting element is advanced distally along the first and second jaws.

In another embodiment, a surgical device is provided for grasping and cutting tissue. The device includes an end effector having first and second jaws configured to move relative to one another between an open position in which the jaws are spaced apart and a closed position in which the jaws are configured to engage tissue therebetween, and a handle assembly coupled to the end effector. The handle assembly can include a closure actuator configured to move the jaws between the open and closed positions, a firing actuator configured to advance a cutting member distally along the jaws to cut tissue engaged between the first and second jaws, and a blocking member configured to extend across a finger recess in the firing actuator when the jaws are in the open position to thereby prevent access by a user to the firing actuator. The blocking member can be configured to move away from the finger recess when the jaws are moved to the closed position.

The device can have a variety of configurations. For example, the closure actuator can form a first handle member of the handle assembly, and the firing actuator can be mounted on a second handle member of the handle assembly, with the first and second handle members being pivotally coupled to one another. In one embodiment, the blocking member can be pivotally mounted on the second handle member. In another embodiment, the blocking member can be linearly slidably mounted on the second handle member.

In another embodiment, the device can include a linkage member coupled between the blocking member and the first actuator. In one embodiment, the linkage member can be configured to exert a distally directed force on the blocking member when the closure actuator is actuated to move the jaws from the open position to the closed position. In another embodiment, the linkage member can be configured to move the blocking member away from the finger recess when the jaws are moved to the closed position.

Methods for actuating a surgical device are also provided and in one embodiment, the method includes moving a closure actuator on a surgical device from a first position to a second position to cause first and second jaws of the surgical device to move from an open configuration in which the jaws are spaced apart to a closed configuration in which the jaws grasp tissue therebetween. Moving the closure actuator from the first position to the second position can move a blocking member from a first position, in which the blocking member extends across a finger recess of the firing actuator such that the blocking member is inaccessible to a user, to a second position, in which the blocking member is moved away from the finger recess such that the finger recess is accessible to a user. With the jaws in the closed position, the firing actuator on the surgical device can be moved to advance a cutting assembly along the first and second jaws to thereby cut the tissue grasped therebetween, the firing actuator being inaccessible to a user when the closure actuator is in the first position. The blocking member can move in various ways. For example, in one embodiment, the blocking member pivots from the first position to the second position. In another embodiment, the blocking member slides longitudinally from the first position to the second position. The method can also include applying RF energy to tissue grasped between the first and second jaws, and/or delivering one or more staples to the tissue.

A surgical device is also provided herein that includes an end effector having first and second jaws configured to move relative to one another between an open position in which the jaws are spaced a distance apart from one another and a closed position in which the jaws are configured to grasp tissue therebetween. The handle portion can include a first actuator operatively associated with the first and second jaws and movable between a first position and a second position, movement of the actuator from the first position to the second position being effective to move the jaws from the open position to the closed position, and a second actuator configured to advance a cutting element distally along the first and second jaws to cut tissue grasped therebetween. The second actuator can be coupled to a torsion spring that biases the second actuator to a first inaccessible position in which the second actuator cannot be manually actuated by a user. When the first actuator is in the first position and the jaws are in the open position, the second actuator is in the first inaccessible position, and movement of the first actuator from the first position to the second position is effective to overcome the biasing force and move the second actuator to a second accessible position in which the second actuator can be manually actuated by a user.

A method for actuating a surgical device is also provided and includes moving a closure actuator on a surgical device from a first position to a second position to cause first and second jaws of the surgical device to move from an open configuration in which the jaws are spaced apart to a closed configuration in which the jaws grasp tissue therebetween. With the jaws in the closed position, moving a firing actuator on the surgical device can advance a cutting assembly along the first and second jaws to thereby cut the tissue grasped therebetween. When the closure actuator is in the first position, the firing actuator is pivoted away from an opening formed in a handle on the surgical device so that it is inaccessible to a user, and moving the closure actuator to the second position is effective to move the firing actuator into the opening formed in the handle to thereby allow a user to access the firing actuator.

Another embodiment of a surgical device is provided and includes an end effector having first and second jaws configured to move relative to one another between an open position in which the jaws are spaced a distance apart from one another and a closed position in which the jaws are configured to grasp tissue therebetween. The device can include a handle portion having a first actuator operativelly associated with the first and second jaws and movable between a first position and a second position, movement of the actuator from the first position to the second position being effective to move the jaws from the open position to the closed position, and a second actuator configured to advance a cutting element distally along the first and second jaws to cut tissue grasped therebetween. When the first actuator is in the first position and the jaws are in the open position, the second actuator is partially disposed in a recess formed in the first actuator, and when the first actuator moves from the first position to the second position, a mating feature on the first actuator is configured to engage the second actuator to move the second actuator to a second accessible position.

Yet another embodiment of a surgical device is provided and can include an end effector having first and second jaws configured to move relative to one another between an open position in which the jaws are spaced a distance apart from one another and a closed position in which the jaws are configured to grasp tissue therebetween. The device can include a handle portion having a first actuator operatively associated with the first and second jaws and movable between a first position and a second position, movement of the actuator from the first position to the second position being effective to move the jaws from the open position to the closed position. A second actuator can be configured to advance a cutting element distally along the first and second jaws to cut tissue grasped therebetween. When the first actuator is in the first position and the jaws are in the open position, the second actuator is recessed within the first actuator in a first inaccessible position so that the second actuator cannot be manually actuated by a user.

A method for actuating a surgical device is also provided and includes moving a closure actuator on a surgical device from a first position to a second position to cause first and second jaws of the surgical device to move from an open configuration in which the jaws are spaced apart to a closed configuration in which the jaws grasp tissue therebetween. With the jaws in the closed position, moving a firing actuator on the surgical device can advance a cutting assembly along the first and second jaws to thereby cut the tissue grasped therebetween. The firing actuator is disposed within the closure actuator in a first inaccessible position when the closure actuator is in the first position, and moving the closure actuator to the second position is effective to expose the firing actuator.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical devices are provided having lockout mechanisms for preventing premature actuation of a cutting mechanism. These surgical devices generally include a handle and an effector disposed at a distal end of device and configured to grasp tissue. In certain aspects, the end effector can include first and second jaws that can move from an open position to a closed position in which the jaws grasp tissue therebetween. Such devices can further include a firing actuator configured to advance and retract a cutting mechanism for severing tissue grasped by the end effector. When the jaws of the end effector are in an open position, the firing actuator can be inaccessible to a user to prevent the user from prematurely engaging the firing actuator, i.e. engaging the firing actuator before tissue is grasped by the end effector. When the jaws of the end effector are in the closed position with tissue grasped therebetween, the firing actuator can be accessible to a user to allow actuation of the cutting mechanism to thereby cut, seal, and or apply energy to the tissue grasped by the end effector.

Figure 1A:
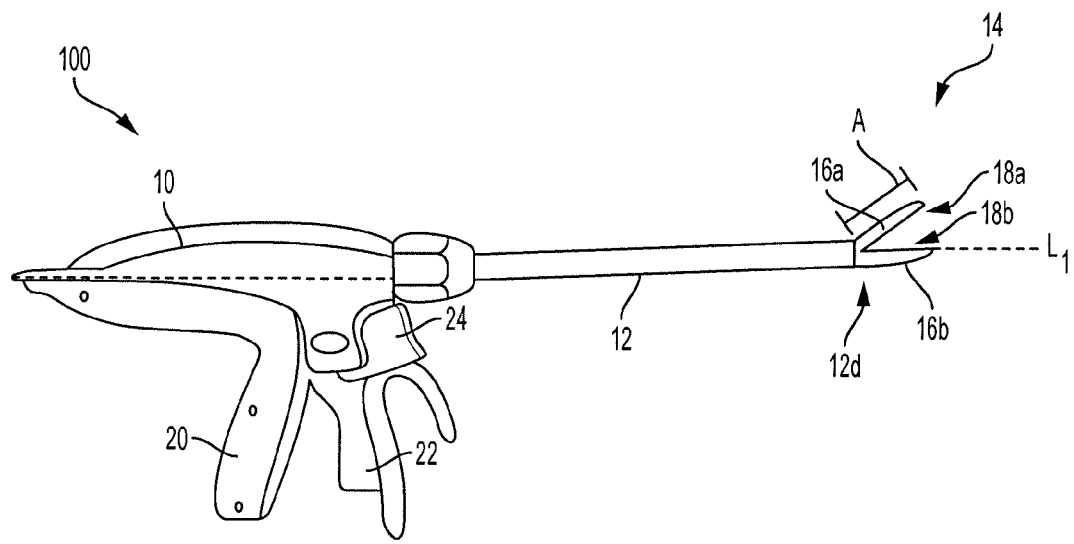
FIG. 1A is a side view of a surgical device that includes an end effector, a shaft, and a handle.

FIG. 1A illustrates one embodiment of a surgical device configured to grasp and cut tissue. The illustrated surgical device 100 generally includes a proximal handle portion 10, a shaft portion 12, and an end effector 14 for grasping tissue. The illustrated proximal handle portion 10 has a pistol-style configuration with actuators located for engagement by a user's fingers. In particular, the proximal handle portion 10 includes a stationary grip 20 and a closure grip 22 pivotally mounted thereto. The closure grip 22 is movable toward and away from the stationary grip 20 to adjust a position of the end effector 14. The shaft portion 12 extends distally from the proximal handle portion and can have a lumen (not shown) extending therethrough for carrying mechanisms for actuating the end effector 14. A person skilled in the art will appreciate that while FIG. 1A illustrates a surgical device having a pistol-style handle, the handle can have a variety of other configurations including a scissor-style handle, in which one or both actuators are pivotally movable toward and away from one another, or any other style of handle known in the art.

The end effector can have a variety of sizes, shapes, and configurations. As shown in FIG. 1A, the end effector 14 can include first and second jaws 16a, 16b disposed at a distal end 12d of the shaft portion 12. The end effector 14 can include a first, upper jaw 16a and second, lower jaw 16b which can be configured to close or approximate about an axis. Both of the jaws 16a, 16b can be moveable relative to the shaft portion 12 or alternatively a single jaw can pivot so that the end effector 14 can move between a first, open position in which the jaws 16a, 16b are positioned a distance apart to a second, closed position in which the jaws 16a, 16b are moved toward one another and are substantially opposed. When the jaws 16a, 16b are in the second, closed position (not shown), a longitudinal axis of the first jaw 16a can be substantially parallel to a longitudinal axis of the second jaw 16b and the jaws 16a, 16b can be in direct contact. In the illustrated embodiment, the first jaw 16a can pivot relative to the shaft portion 12 and to the second jaw 16b while the second jaw 16b remains stationary. The jaws 16a, 16b can have a substantially elongate and straight shape, as shown in FIG. 1A, but a person skilled in the art will appreciate that one or both of the jaws 16a, 16b can be curved about a longitudinal axis thereof. The jaws 16a, 16b can have any suitable axial length for engaging tissue, where the axial length is measured along a longitudinal axis $L_1$ of the shaft portion. The axial length A of the jaws 16a, 16b can also be selected based on the targeted anatomical structure for cutting and/or sealing.

The jaws 16a, 16b can have any combination of features configured to facilitate grasping tissue therebetween. The first jaw 16a can have a first inner engagement surface and the second jaw 16b can have a second inner engagement surface, both of the first and second engagement surfaces 18a, 18b being configured to directly contact tissue. Either one or both of the engagement surfaces can include one or more surface features (not shown) formed thereon that can help secure the tissue thereon. For example, the surface features can include various surface features, such as teeth, ridges, or depressions, configured to increase friction between the tissue and the engagement surfaces of the jaws 16a, 16b without tearing or otherwise damaging the tissue in contact with such surface features. The first and second jaws 16a, 16b can optionally include features for interacting with a compression member configured to move within the jaws 16a, 16b and to apply a compressive force on tissue.

Figure 1B:
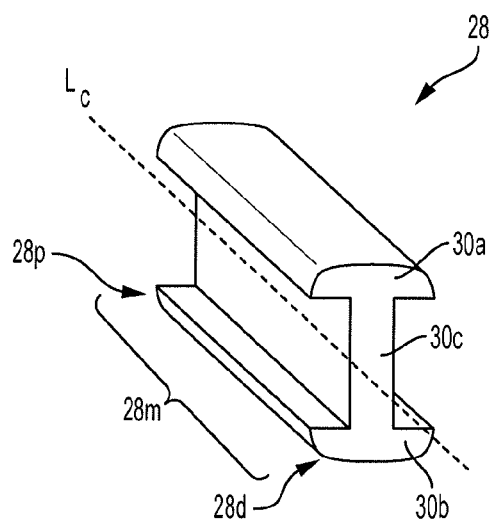
FIG. 1B is a perspective view of an I-beam for closing the jaws of the device of FIG. 1A and having a cutting member formed thereon.

The surgical device 100 can optionally include a compression member having various sizes, shapes, and configurations. In general, the compression member can have an elongate shape and can be moveable proximally and distally along the longitudinal axis $L_1$ of the shaft portion and the end effector. An exemplary compression member 28 is illustrated in FIG. 1B. As shown, the compression member 28 can have a proximal end 28p, a medial portion 28m, and a distal end 28d. The proximal end 28p and the medial portion 28m of the compression member 28 can be sized and shaped to reciprocate within the shaft portion 12 of the device 100, while the distal end 28d of the compression member 28 can be sized and shaped to interact with the jaws 16a, 16b of the end effector 14. A longitudinal axis $L_C$ of the compression member 28 can be aligned and coaxial with longitudinal axis of the shaft portion 12, though other configurations are possible. The compression member 28 can be actuatable from the proximal handle portion of the instrument by any suitable mechanism that is operatively coupled to the proximal end 28p of the compression member 28, such as via the firing actuator 24 shown in FIG. 1A. The compression member 28 can include a connecting portion 30c and upper and lower flanges 30a, 30b thus providing an "I-beam" type cross-sectional shape at the distal end 28d of the compression member 28. In the illustrated embodiment, the upper and lower flanges 30a, 30b are positioned substantially perpendicular to the connecting portion 30c to form the "I-beam" shape. As previously mentioned, the upper and lower flanges 30a, 30h are sized and shaped to slide in the recessed slots in each of the first and second jaws 16a, 16b, and this sliding contact of lateral edges of the flanges 30a, 30b and sides of each of the recessed slot portions prevents lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the shaft portion 12.

The device 100 can include a cutting member (not shown) configured to transect tissue captured between the jaws, and the cutting member can vary in any number of ways. The cutting member can be sized and shaped to transect or cut various thicknesses and types of tissue positioned between the jaws of the end effector. In an exemplary embodiment, the cutting member is positioned at the distal end 28d of the compression member 28, formed on the connecting portion 30c of the compression member 28. The cutting member can have a sharp or serrated edge configured to transect the tissue. In an exemplary embodiment, the cutting member can be recessed relative to distal ends of upper and lower flanges 30a, 30b of the I-beam compression member 28 so that compression occurs prior to transecting or cutting of the tissue. As will be appreciated by a person skilled in the art, in another embodiment the cutting member can be a knife blade that is not attached to a compression member such that the cutting member can advance and retract relative to the jaws without applying compression to the tissue.

Referring back to FIG. 1A, the surgical device 100 can have a closure actuator, i.e., closure grip 22 that can be configured to open and close the jaws 16a, 16b of the end effector 14. Manipulation of the closure grip 22 can pivot or otherwise move the jaws relative to one another such that the jaws can engage tissue, move anatomical structures, or perform other surgical functions. The closure grip 22 can be moveable toward and away from stationary grip 20, such as via pivoting. In particular, the closure grip 22 can have a first position in which it is angularly offset from the stationary grip 20 and the jaws 16a, 16b of the end effector 14 are open. The closure grip 22 can have a second position where it is positioned adjacent to or substantially in contact with the stationary grip 20 and the jaws 16a, 16b of the end effector 14 can engage tissue and apply a force to tissue disposed therebetween. The closure grip 22 can be biased to the first open position with the jaws 16a, 16b of the end effector 14 being open, as shown in FIG. 1. The closure grip 22 can move the jaws 16a, 16b between the open and closed positions using manual or powered components. For example, in manually actuated embodiments, the closure grip 22 can be coupled to a gear that interacts with a rack extending through the handle and manual movement of the closure grip 22 toward the stationary grip 20 can move the rack distally toward the end effector 14, causing a closure rod extending through the shaft to exert a force onto the jaws 16a, 16b to close the jaws 16a, 16b. In powered embodiments, a motor can be disposed in the proximal handle portion 10 and manual movement of the closure grip 22 can cause a control signal to be sent to the motor, which drives a closure rod to cause the jaws 16a, 16b to close. The closure grip 22 can interact with one or more locking features (not shown) configured to lock the closure grip 22 relative to the stationary grip 20. For example, the locking feature can automatically engage when the closure grip 22 substantially contacts the stationary grip 20 or the locking feature can automatically engage at each position the closure grip 22 is pivoted through, such as via ratcheting.

In certain aspects, the surgical device can have a second, firing actuator that can be separate from a first, closure actuator. The firing actuator can be configured to advance a cutting member, apply energy to tissue, or both. The firing actuator can have various sizes, shapes, and configurations but in illustrated embodiment, firing actuator 24 includes a button or switch that can be depressed by a user. In another embodiment, the firing actuator 24 can include a trigger, switch, etc. that can be pivoted or otherwise moved relative to the proximal handle portion 10 by a user. Depressing or pivoting the firing actuator 24 can cause the cutting member to advance toward the effector 14. For example, depressing or pivoting the firing actuator can cause the compression member and/or the cutting member to advance distally and/or retract proximally relative to the jaws 16a, 16b. In powered embodiments, the firing actuator 24 can be in electrical communication with a motor (not shown) disposed in the proximal handle portion 10. The motor can be operatively coupled to the compression member 28 using known components, such as a gear and rack. In these embodiments, activation of the motor can thus advance and/or retract the compression member 28 relative to the jaws 16a, 16b. The firing actuator 24 can also be used to perform other functions, such as to activate the delivery of energy to the opposed jaws, and/or cause one or more clips or staples to be delivered into the tissue.

Where the surgical device 100 is configured to apply energy to tissue, the surgical device 100 can include a generator (not shown) that can be operatively coupled to the firing actuator 24. The generator can be any suitable generator known in the art, such as an RF generator. The generator can be a separate unit that is electrically connected to the surgical device 100 to decrease a weight and size profile of the device 100. A bore of the shaft portion 12 can carry electrical leads or wires that can deliver electrical energy to components of the end effector 14. As will be appreciated by persons skilled in the art, the surgical devices described below can also be configured to apply energy to tissue and can include any of the components described above, such as a generator and a compression member.

Figure 2A:
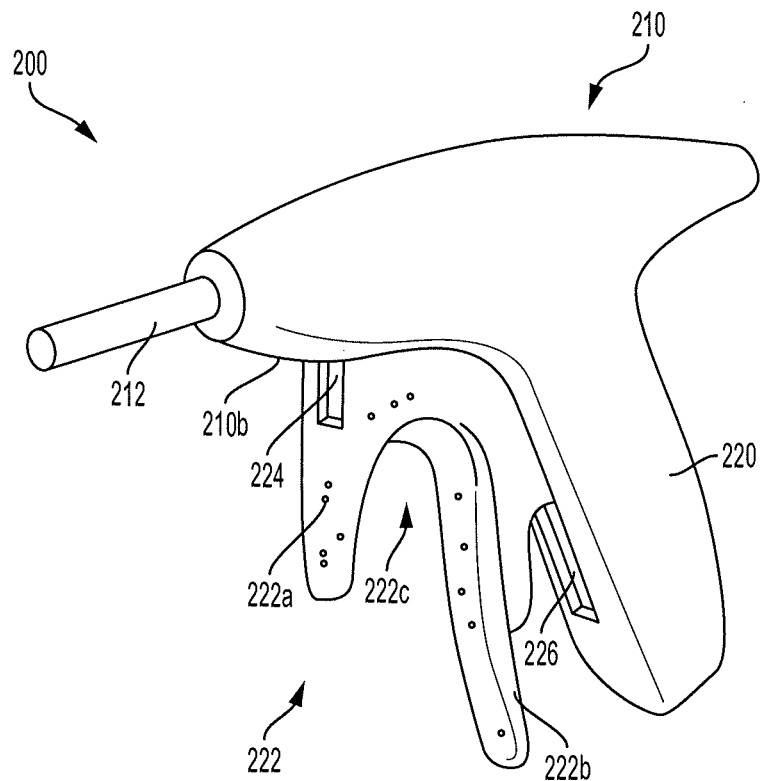
FIG. 2A is a perspective view of an embodiment of a handle assembly for use with the device of FIG. 1A, showing a first actuator in an inaccessible position.
Figure 2B:
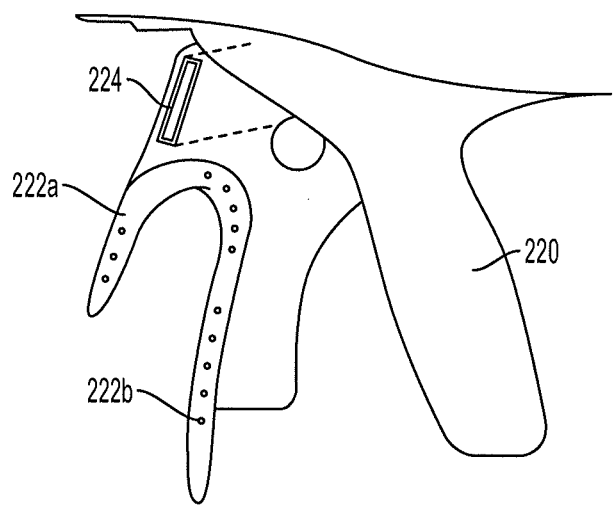
FIG. 2B is a side, semi-transparent view of the actuators of FIG. 2A.
Figure 2C:
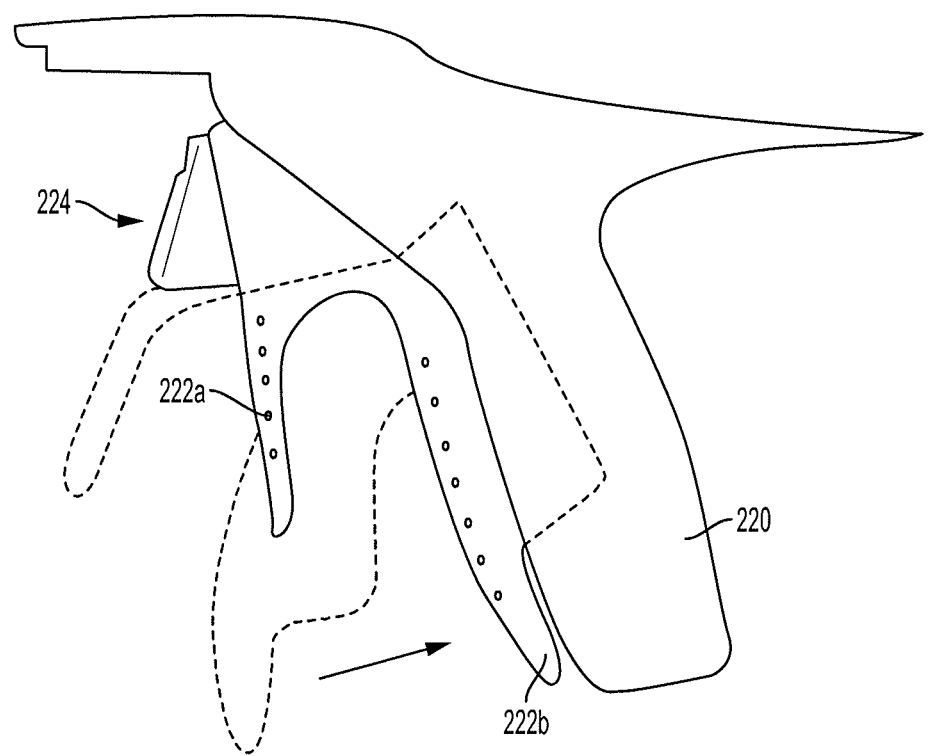
FIG. 2C is a side view of the actuators of FIG. 2A illustrating how movement of the first actuator exposes the second actuator such that the second actuator is in an accessible position.

FIGS. 2A-2C illustrate an embodiment of the handle portion of the surgical device of FIG. 1A, modified to prevent premature actuation of the firing actuator. As shown in FIG. 2A, the device 200 includes a closure grip 222 that is configured to move toward and away from a stationary grip 220. The closure grip 222 can have a contoured shape for grasping by a user. In the illustrated embodiment, the closure grip 222 has a body with first and second arms 222a, 222b extending therefrom. As shown, the first and second arms 222a, 222b define a substantially U-shaped recess 222c for grasping by a user. The device 200 further includes a firing actuator 224 that is positioned adjacent to a bottom surface 210b of the proximal handle portion 210 and within a recess formed in a distal-facing surface of the first arm 222a of the closure actuator. The firing actuator 224 can have a variety of sizes, shapes, and configurations, but in the illustrated embodiment it has a substantially rectangular cross-sectional shape that includes a distal-facing surface that can be contacted by one or more of a user's finger. The stationary grip 220 can have a cavity 226 formed therein that is configured to receive a proximal portion of the closure grip 222 as the closure grip 222 is moved toward the stationary grip 220. The surgical device 200 can have a first position in which the end effector (not shown) is in an open configuration with the jaws spaced apart. When the device 200 is in the first position, as shown in FIGS. 2A and 2B, the firing actuator 224 can be positioned substantially inside of the recess in the closure grip 222 such that the firing actuator 224 is inaccessible and cannot be actuated by a user. With the device 200 so positioned, the closure grip 222 can be spaced a distance apart from the stationary grip 220. The surgical device 200 can have a second position in which the end effector (not shown) is in a closed configuration with the jaws substantially opposed and configured to grasp tissue therebetween. When the device 200 is in this closed position, as shown in FIG. 2C, the proximal portion of the closure grip 222 can be positioned in the cavity 226 of the stationary grip 220 and the second arm 222b of the closure grip 222 can directly contact and be positioned adjacent to the stationary grip 220. The firing actuator 224 can remain substantially stationary as the closure grip 222 moves proximally from the first position to the second position. As a result, this movement will cause the firing actuator 224 to extend out of the recess in the closure grip 222 and be in an accessible position when the closure grip 222 is adjacent to the stationary grip 220, as shown in FIG. 2C. The device can include one or more mechanisms (not shown) configured to move the firing actuator 224 back into the recess in the closure grip 222 after a user engages and actuates the firing actuator 224 so that the firing actuator 224 is inaccessible to a user.

FIGS. 3-7 illustrate additional embodiments of a device in which the firing actuator is inaccessible when the jaws are in an open position. In these embodiments, the device has a scissor-style handle, however, the mechanisms for rendering the firing actuator inaccessible can be used with other handle styles. In general, the scissor-style devices have first and second elongate members. A proximal end of a first elongate member can form the stationary grip and a proximal end of the second elongate member can form the closure grip, while distal ends of each of the first and second elongate members can define the jaws. Referring first to FIG. 3A, the device 300 includes a stationary grip 320, a closure grip 322, and an end effector 314. The stationary grip 320 and the closure grip 322 can be pivotably coupled together at a pivot point 330. Thus, while grip 320 is referred to as a "stationary" grip, a person skilled in the art will appreciate that one and/or both grips can move relative to one another. As shown in FIG. 3A, the pivot point 330 can be positioned toward the jaws 316a, 316b such that an axial length of the first and second jaws 316a, 316b can be between about 20 to 30% of an axial length of the closure grip 322 and of the stationary grip 320, the axial length being measured along a longitudinal axis thereof. The closure grip 322 can have a terminal distal end that is a jaw 316b and the stationary grip 320 can have a terminal end that forms a first jaw 316a. A first terminal end of the closure grip 322 can define the first jaw 316b while a second terminal end of the closure grip 322 can include an actuation surface or opening configured to be grasped by a user, such as a closure finger hole 322p that can receive a user's thumb. Similarly, a first terminal end of the stationary grip 320 defines a second jaw 316a and a second terminal end of the stationary grip 320 also includes an opening configured to be grasped by a user, e.g. a stationary finger hole 320p that can receive one or more of a user's fingers.

The device 300 can further include a firing actuator 324 mounted on the stationary grip 320 for actuating the cutting mechanism relative to the jaws 316a, 316b. As in the previous embodiments, the firing actuator can be configured to advance and retract a cutting member toward and away from the jaws. As shown, the firing actuator 324 can include a slider 332 coupled to the stationary grip 320. The slider 332 can be shaped as a plate that can slide proximally and distally relative to the stationary grip 320 to actuate a cutting member. The slider 332 can have a ring-shaped opening 334 formed in a distal end 332d thereof that can receive one or more of a user's fingers therethrough. The ring-shaped opening 334 has a substantially circular shape, but a person skilled in the art will appreciate that the ring-shaped opening 334 can have an elliptical, square, rectangular, or any other shape that can receive one or more of a user's fingers therethrough. The slider 332 can optionally be coupled to a biasing spring 336 that biases the slider 332 distally relative to the stationary grip 320. For example, the biasing spring 336 can be located in a proximal portion of the stationary grip 320 and can have proximal and distal ends 336p, 336d, the distal end 336d of the biasing spring 336 being coupled to a proximal end 332p of the slider 332 and biasing the slider 332 distally.

Figure 3A:
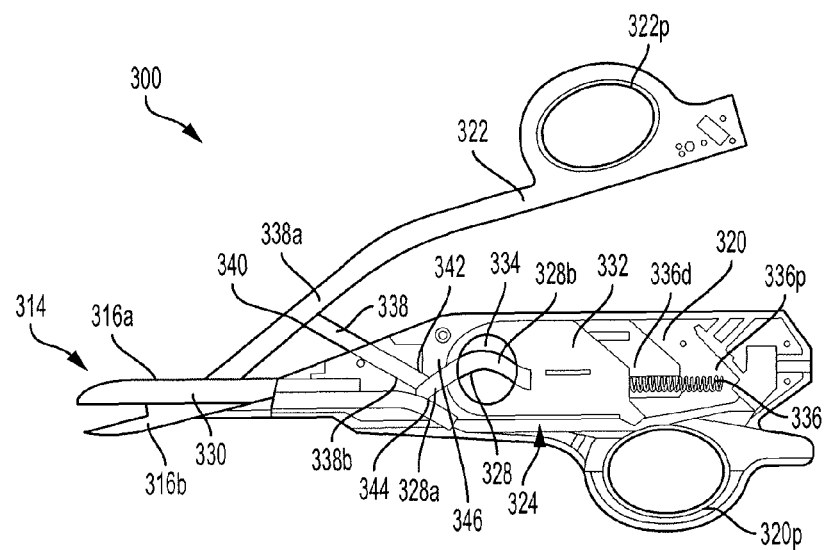
FIG. 3A is a side view of another embodiment of a surgical device having first and second actuators with a blocking arm extending across the second actuator when the jaws are in an open position.
Figure 3B:
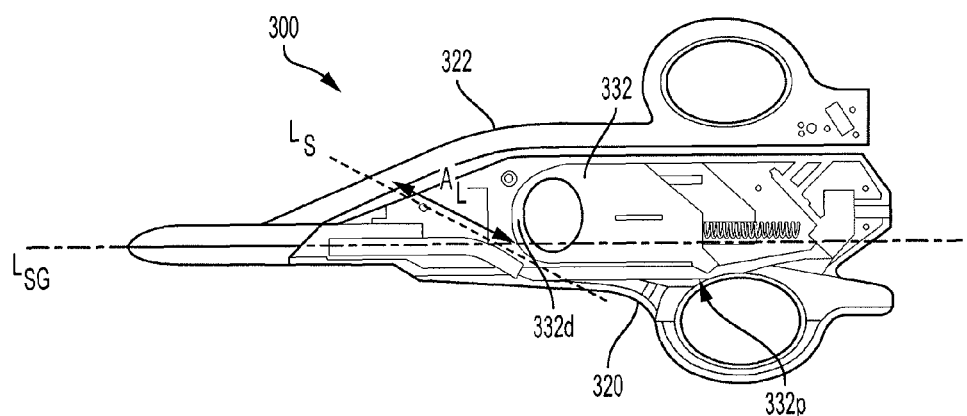
FIG. 3B is a side view of the device of FIG. 3A with the blocking arm moved away from the second actuator such that the second actuator is in an accessible position when the jaws are in a closed position.

As further shown in FIGS. 3A and 3B, the device 300 can include a blocking arm 328 that extends across the ring-shaped opening 334 of the firing actuator 324 so that the firing actuator 324 is inaccessible to a user. While only a single blocking arm 328 is illustrated, a person skilled in the art will appreciate that a second, identical blocking arm can be disposed on an opposite side of the device (not shown). In this configuration, the blocking arms can obstruct both sides of the ring-shaped opening 334 so that it is inaccessible to a user when the device 300 is in an open position, i.e., when, the closure grip 322 is spaced a distance apart from the stationary grip 320 and the jaws are in the open position. The blocking arm can have a variety of sizes, shapes, and configurations. In general, the blocking arm 328 has a first portion 328a configured to interact with the second terminal end of the linkage and a second portion 328b configured to extend across the ring-shaped opening 334 of the firing actuator 324. The first portion 328a of the blocking arm 328 can have an elongate shape and a length that is smaller than a length of the second portion 328b. The first portion 328a of the blocking arm can be substantially perpendicular to the second portion 328b and the blocking arm can include a bore (not shown) formed therein between the first portion 328a and the second portion 328b. The bore can receive a pin (not shown) therein for pivotably coupling the blocking arm to the stationary grip at a pivot point 346. The second portion 328b of the blocking arm 328 can be curved and can have a radius of curvature substantially equal to a radius of curvature of the ring-shaped opening 334 so that the blocking arm 328 can be positioned along an outer circumference of the ring-shaped opening 334, as shown in FIG. 3B.

The device 300 can further include an elongate linkage 338 that extends between the closure grip 322 and the stationary grip 320 and facilitates movement of the closure grip relative to the stationary grip 320. More specifically, the elongate linkage 338 can extend between the slider 332 and the closure grip 322 and can have first and second terminal ends 338a, 338b, the first terminal end 338a being coupled to the closure grip 322 at a pivot point 340 that is proximal to the pivot point 330, and the second terminal end 338b being slidably coupled to the stationary grip 320. The second terminal end 338b of the elongate linkage 338 can include a pin 342 that extends through a slot 344 formed in the stationary grip 320, the pin 342 being configured to slide along a length of the slot 344. The slot 344 can have a generally elongate shape and a longitudinal axis of the slot $L_S$ can be angularly offset from a longitudinal axis of the stationary grip $L_{SG}$, as shown in FIG. 3B. An axial length (not shown) of the slot 344 and an axial length $A_L$ of the elongate linkage 338 can be selected so that the elongate linkage does not interfere with and prevent the device from having a closed position in which the closure grip 322 is positioned adjacent to the stationary grip 320, as shown in FIG. 3B.

A relative positioning of the pivot point 346, the blocking arm 328, the slot 344, and the elongate linkage 338 can affect movement of the blocking arm 328 relative to the ring-shaped opening 334. When the device 300 is in the first open position, the pivot point 346 can be positioned adjacent to or alternatively, directly in contact with the second terminal end 338b of the elongate linkage 338, as shown in FIG. 3A. As the closure grip 322 is moved toward the stationary grip 320, the pin on the second terminal end 338b of the elongate linkage 338 can move within the slot 344 in a generally proximal direction and can contact the first portion 328a of the blocking arm 328 and pivot the first portion 328a proximally about the pivot point 346. This can cause the second portion 328b of the blocking arm 328 to pivot distally in a counter-clockwise direction, moving the second portion 328b toward the outer circumference of the ring-shaped opening 334 until the device 300 is in the closed position of FIG. 3B. When the device 300 is so positioned, the second portion 328b of the blocking arm 328 can extend along the outer circumference of the ring-shaped opening 334 so that the ring-shaped opening 334 is substantially unobstructed and a user can insert one or more fingers therethrough, as shown in FIG. 3B. After a user engages and actuates the firing actuator 324, a biasing force can automatically move the closure grip 322 away from the stationary grip 320 and open the first and second jaws 316a, 316b.

The pin on the second terminal end 338b of the elongate linkage 338 can then move away from the blocking arm 328, within the slot 344, and the second portion 328b of the blocking arm 328 can automatically pivot back into the position shown in FIG. 3A in which the firing actuator 324 is inaccessible to a user.

Figure 4A:
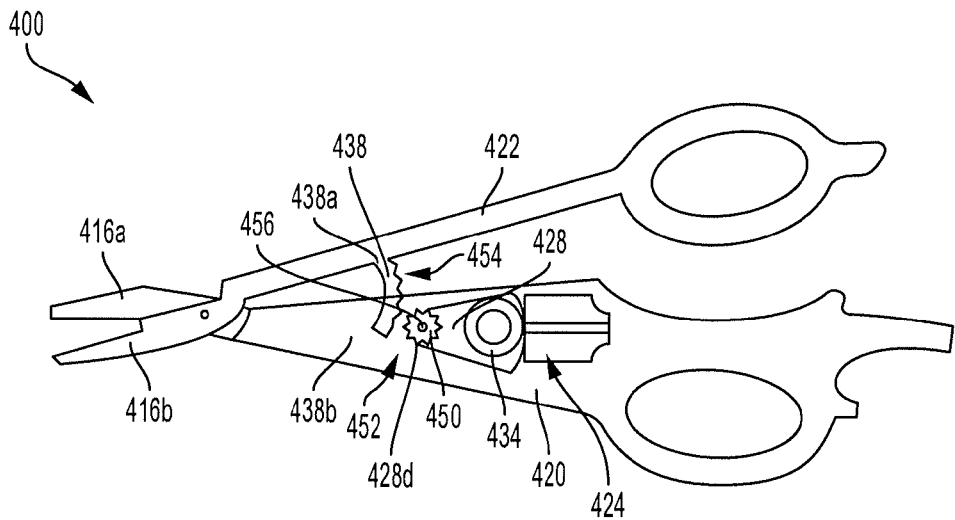
FIG. 4A is a side view of another embodiment of a surgical device having first and second actuators, showing the second actuator in an inaccessible position when the jaws are in an open position.
Figure 4B:
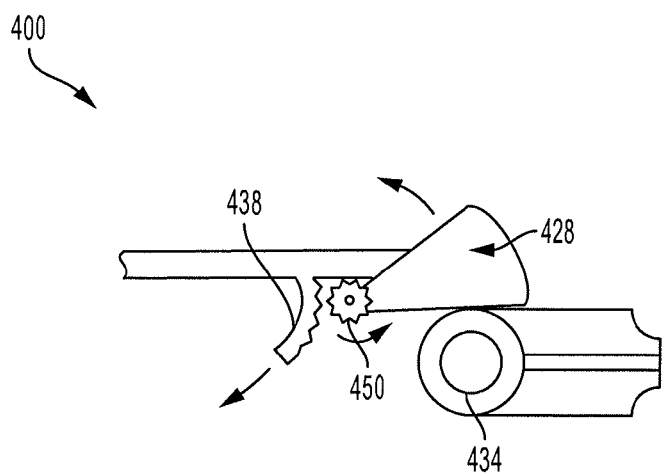
FIG. 4B is a side view of the device of FIG. 4A showing the second actuator in an accessible position when the jaws are in a closed position.

FIGS. 4A and 4B illustrate another embodiment of a surgical device 400 having a blocking shield 428 configured to cover a firing actuator 424. While a single blocking shield 428 is illustrated, a person skilled in the art will appreciate that a second, identical blocking shield can be disposed on an opposite side of the device (not shown) so that both sides of the firing actuator can be obstructed and inaccessible to a user. The blocking shield can have various sizes, shapes, and configurations. In the illustrated embodiment, the blocking shield 428 has a substantially triangular cross-sectional shape taken along a longitudinal axis of the device 400. The blocking shield 428 can have a relatively small thickness (not shown) measured in a direction perpendicular to a longitudinal axis of the stationary grip 420. The blocking shield 428 can have various sizes and shapes selected so that when the device 400 is in the open position, the blocking shield 428 can cover a ring-shaped opening 434 of the firing actuator 424, thus making it inaccessible to a user. In the illustrated embodiment, a distal end 428d of the blocking shield 428 can be pivotably coupled to the stationary grip 420 at a pivot point 456. As shown, the blocking shield 428 can be coupled to a gear 450 such that the blocking shield 428 and the gear 450 can rotate as a unit. The gear 450 can have various configurations, but it is preferably a pinion having teeth 452 formed on an outer circumference thereof. As in the previous embodiment, the device 400 can include an elongate linkage 438 having a first terminal end 438a coupled to the closure grip 422. As shown in FIGS. 4A and 4B, the linkage 438 can have a curved shape and a proximal-facing surface can have teeth 454 formed thereon that can mate with the teeth 452 formed on the pinion gear 450. When the device 400 is in the first position, the teeth 454 of the linkage 438 can be in contact with the teeth 452 of the pinion 450. As the closure grip 422 is moved toward the stationary grip 420, the linkage 438 can move along an arc-shaped path toward the stationary grip 420, and this can cause the pinion 450 to rotate, as shown in FIG. 4B. Because the pinion 450 and the blocking shield 428 move as a unit, rotation of the pinion 450 causes the blocking shield 428 to pivot about the pivot point 456, thereby exposing the ring-shaped opening 434 of the firing actuator 424 and allowing a user to access it. When the device 400 is in this position, the blocking shield 428 is preferably positioned away from the ring-shaped opening 434 of the firing 424 actuator. The firing actuator 424 is thus substantially unobstructed so that a user can insert one or more fingers through the ring-shaped opening 434 of the firing actuator 424. After a user engages and actuates the firing actuator 424, a biasing force can automatically move the closure grip 422 away from the stationary grip 420 and open the first and second jaws 416a, 416b. This can also cause the blocking shield(s) to pivot into the position shown in FIG. 4A in which the firing actuator 424 is inaccessible to a user.

Figure 5:
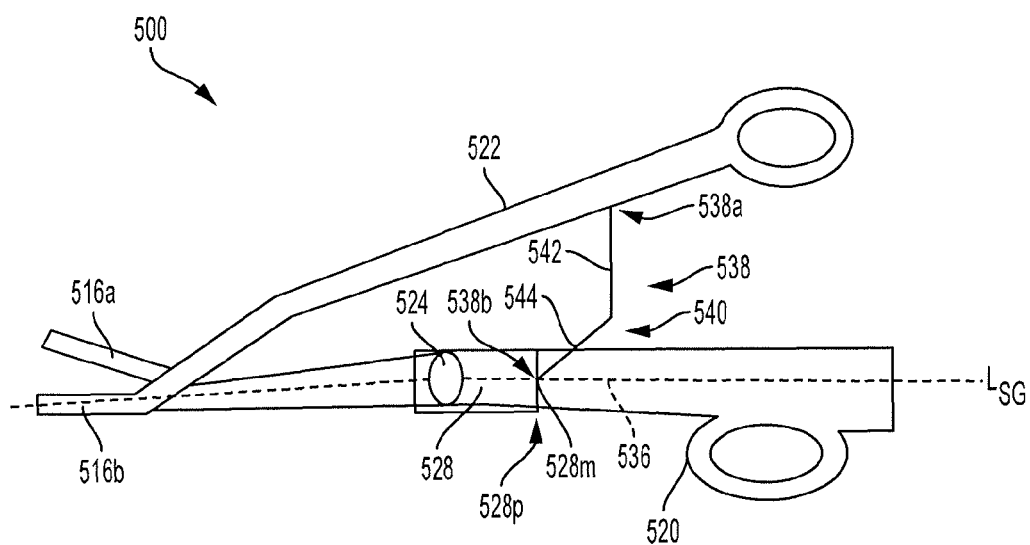
FIG. 5 is a side view of another embodiment of a surgical device having first and second actuators, showing the second actuator in an inaccessible position when the jaws are in an open position.

FIG. 5 illustrates another embodiment of a surgical device 500 having a blocking shield 528 configured to cover a firing actuator 524. While only a single blocking shield 528 is illustrated, a person skilled in the art will appreciate that a second, identical blocking arm can be disposed on an opposite side of the device (not shown) so that both sides of the firing actuator can be obstructed and made inaccessible to a user. In this embodiment, the blocking shield 528 has a substantially rectangular cross-sectional shape, the cross-section being taken along the longitudinal axis $L_{SG}$ of the stationary grip 520. As shown, the blocking shield 528 can be configured to move proximally and distally along the longitudinal axis $L_{SG}$ of the stationary grip 520 via an elongate linkage 538. The elongate linkage 538 can extend between the blocking shield 528 and the closure grip 522, as shown. More specifically, a first terminal end 538a of the elongate linkage 538 can be coupled to the closure grip 522 and a second terminal end 538b of the elongate linkage 538 can be coupled to a proximal end 528p of the blocking shield 528. Preferably, the second terminal end 538b of the elongate linkage 538 is positioned below a mid-point 528m of the blocking shield 528 so that the elongate linkage does not obstruct the firing actuator 524 when the blocking shield 528 is positioned proximal or distal to the firing actuator 524. The elongate linkage 538 can have a bend 540 formed therein defining a first portion 542 and a second portion 544. When the device 500 is in the first position, the first portion 542 of the linkage 538 can be positioned substantially perpendicular to the longitudinal axis $L_{SG}$ of the stationary grip 520, while the second portion 544 of the linkage 538 can be positioned at an angle relative to the longitudinal axis $L_{SG}$. A proximal end of the firing actuator 524 can be coupled to the biasing spring 536 that biases the firing actuator 524 distally in the position of FIG. 5. In use, movement of the closure grip 522 toward the stationary grip 520 can move the second terminal end 538b of the linkage 538 distally along the longitudinal axis $L_{SG}$ of the stationary grip 520. When the closure grip 522 and the stationary grip 520 are substantially opposed and the jaws 516a, 516b are in the closed position, the proximal end 528p of the blocking shield 528 can be positioned distal to the firing actuator 524 such that the firing actuator 524 is accessible to a user and a user can position one or more fingers therethrough. As in the previous embodiments, after a user engages and actuates the firing actuator 524, a biasing force can automatically move the closure grip 522 away from the stationary grip 520 and open the first and second jaws 516a, 516b. This can cause the blocking shield(s) to move proximally to the position shown in FIG. 5 in which the firing actuator 524 is inaccessible to a user. As will be appreciated by a person skilled in the art, the elongate linkage can include first and second linkages joined together by a pin, weld, or any other coupling mechanism known in the art.

Figure 6A:
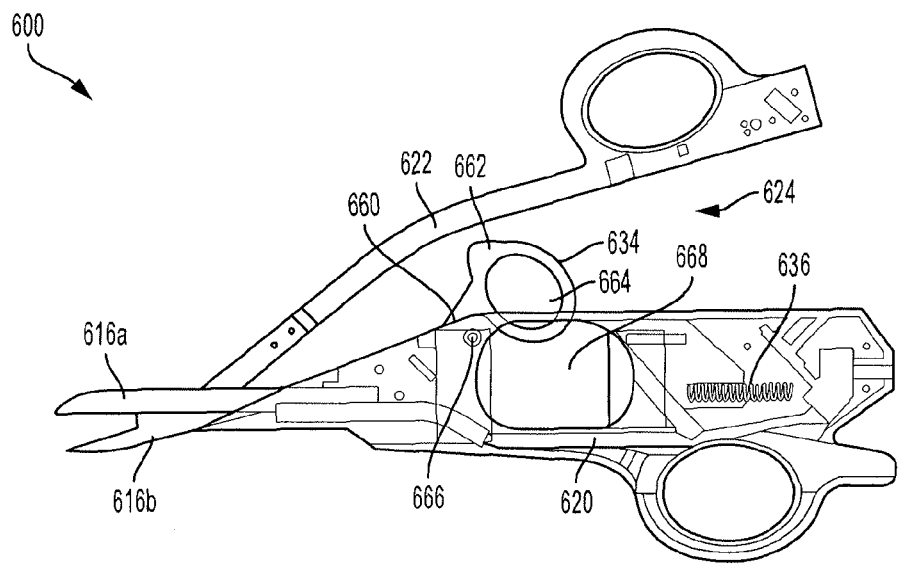
FIG. 6A is a side, semi-transparent view of yet another embodiment of a surgical device having first and second actuators, showing the second actuator in an inaccessible position when the jaws are in an open position.
Figure 6B:
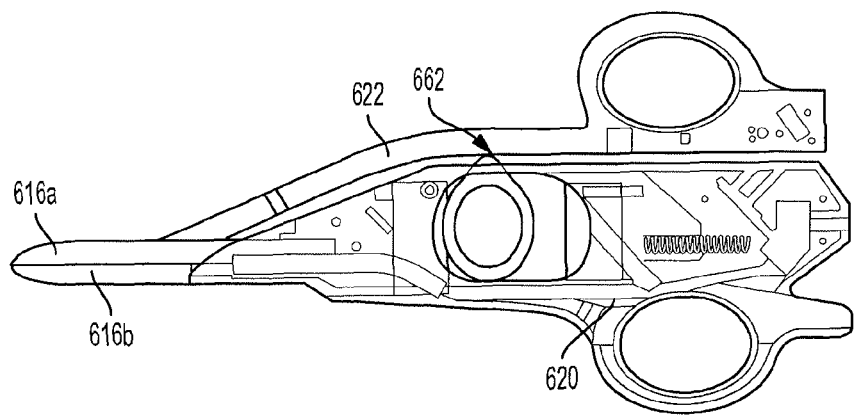
FIG. 6B is a side, semi-transparent view of the device of FIG. 6A, showing the second actuator in an accessible position when the jaws are in a closed position.

FIGS. 6A and 6B illustrate another embodiment of a surgical device 600 having lockout mechanisms configured to prevent premature actuation of a cutting member. In this embodiment, the device 600 includes a pivotable arm 660 having a ring-shaped member 634 integrally formed thereon in a unitary structure, the ring-shaped member 634 including a finger hole 664. In other embodiments, the pivotable arm 660 can be coupled to the ring-shaped member 634 in other ways and need not be integrally formed and have a unitary structure. The finger hole 664 of the ring-shaped member 634 can have a substantially circular shape and can be configured to receive one or more of a user's fingers therethrough. The ring-shaped member 634 of the firing actuator 624 can further include a protrusion 662 formed along an outer circumference thereof that is configured to interact with the closure grip 622, as will be described in greater detail below. A proximal end (not shown) of the pivotable arm 660 can be coupled to a torsion spring 666 disposed in the stationary grip 620. The torsion spring 666 can apply a biasing force that biases the pivotable arm 660 and the ring-shaped member 634 to the position shown in FIG. 6A in which the pivotable arm 660 and ring-shaped member 634 are disposed away from the stationary grip 620 and the jaws are open. The stationary grip 620 can include a recess 668 formed therein for receiving the ring-shaped member 634 of the firing actuator 624 therein and sized so that the firing actuator 624 can move proximally and distally within the recess 668. For example, the recess 668 can have a substantially elliptical shape, but can be shaped in other ways. As shown in FIG. 6A, the device can have a first position in which jaws 616a, 616b are in an open position and the closure grip 622 is positioned at a distance apart from the stationary grip 620. In this first position, the ring-shaped member 634 of the firing actuator 624 is displaced from the recess in the closure grip 622 via the pivotable arm 660 and is inaccessible to a user. At the same time, the protrusion 662 on the ring-shaped member 634 can be positioned between a bottom surface of the closure grip 622 and a top surface of the stationary grip 620. As the closure grip 622 is moved toward the stationary grip 620, a portion of the closure grip 622 can directly contact the protrusion 662 and push the ring-shaped member 634 of the firing actuator 624 toward the recess 668 in the stationary grip 620 until the firing actuator 624 is disposed therein, as shown in FIG. 6B. With the firing actuator 624 so positioned, a user can access the ring-shaped member 634 of the firing actuator 624 and pull it proximally to advance a cutting member (not shown) toward the jaws 616a, 616b to cut tissue grasped by the jaws 616a, 616b. After a user engages and actuates the firing actuator 624, the torsion spring 666 can apply a biasing force to automatically move the closure grip 622 away from the stationary grip 620 and open the first and second jaws 616a, 616b. This can also cause the ring-shaped member 634 of the firing actuator 624 to move to the position shown in FIG. 6A in which the firing actuator 624 is inaccessible to a user.

Figure 7:
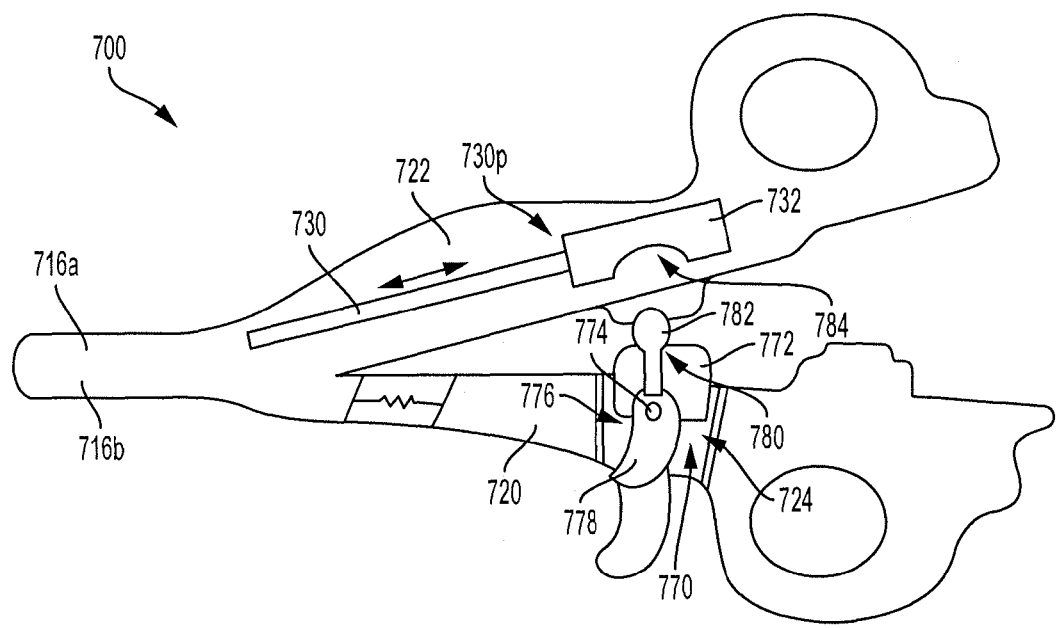
FIG. 7 is side, semi-transparent view of another embodiment of a surgical device having first and second actuators, showing the second actuator movable between an inaccessible position when the jaws are in an open position and an accessible position (shown in phantom) when the jaws are in a closed position.

FIG. 7 illustrates another embodiment of a surgical device 700. In this embodiment, the device 700 includes a firing actuator 724 that can be substantially hidden inside of a channel 770 formed in the stationary grip 720 when the device 700 is in the first position so that the firing actuator 724 is inaccessible. As shown, the channel 770 can be sized and shaped to extend across a width of the stationary grip 720, the width being measured in a direction perpendicular to a longitudinal axis of the stationary grip 720. The channel 770 can optionally include an arm or door (not shown) positioned at a lower surface thereof to contain the firing actuator 724 inside of the channel when the device 700 is in the first position. The channel 770 in the stationary grip 720 can receive a base plate 772 therein that can be configured to slide in a direction that is substantially perpendicular to a longitudinal axis of the stationary grip 720. The firing actuator 724 can be pivotably coupled to the base plate 772 at a pivot point 774. Thus, movement of the base plate 772 can also move the firing actuator 724 relative to the stationary grip 720, as shown. The firing actuator 724 can include a trigger 776 having a first, curved portion 778 configured to be grasped by a user and a second, elongate portion 780 having a mating feature 782 formed on its terminal end. The pivot point 774 coupling the base plate 772 to the trigger 776 can be positioned between the first and second portions 778, 780 of the trigger 776. The device 700 can further include a slider 732 positioned in the closure grip 722 that is coupled to a proximal end 730p of a cutting member 730 and that can be configured to move proximally and distally along a longitudinal axis of the closure grip 722 to advance and retract the cutting member 730. The slider 732 can have a mating recess 784 formed therein for receiving the mating feature 782 of the trigger 776 as the closure grip 722 is moved toward the stationary grip 720. With the trigger 776 so positioned, pivotable movement of the trigger 776 in a proximal direction can move the slider 732 and thus the cutting member 730 distally toward jaws 716a, 716b and then proximally to its original position. After a user engages and actuates the firing actuator 724, a biasing force can automatically move the closure grip 722 away from the stationary grip 720 and open the first and second jaws 716a, 716b. This can also cause the base plate 772 and the firing trigger 776 of the firing actuator 724 to move to the position shown in FIG. 7 in which the firing trigger 776 is inaccessible to a user. A person skilled in the art will appreciate that the device can vary in any number of ways. For example, in the illustrated embodiment, the mating feature 782 has a substantially spherical shape, but the mating feature 782 can be shaped in other ways and can allow the mating feature 782 to press fit or otherwise releasably mate with the mating recess 784 formed in the slider 732.

As will be appreciated by a person skilled in the art, the surgical devices provided herein can be used to perform conventional minimally-invasive and open surgical procedures and can be used in robotic-assisted surgery. A method for cutting tissue is described below and reference is made to the devices of FIGS. 2-7 in turn below.

In use, the surgical device 200 can be inserted in a patient in the second, closed position with jaws (not shown) of the end effector (not shown) closed so as to minimize a size profile of the device 200 during insertion. A user can move the surgical device 200 to the first open position in which the end effector is in an open configuration with the jaws spaced apart and the closure grip 222 spaced a distance apart from the stationary grip 220. When the device 200 is in the first position, as shown in FIGS. 2A and 2B, the firing actuator 224 can be positioned substantially inside of the closure grip 222 such that the firing actuator 224 cannot be actuated by a user. When the jaws of the end effector are positioned adjacent to tissue to be treated, the surgical device 200 can be moved to the second position in which the end effector is in a closed configuration with the jaws substantially opposed and grasping the tissue therebetween. When the device 200 is in the closed position, as shown in FIG. 2C, a proximal portion of the closure grip 222 can be positioned in the recess of the stationary grip 220 and the second arm of the closure grip 222 can directly contact and be positioned adjacent to the stationary grip 220. As the closure grip 222 is moved proximally from the first position to the second position, the firing actuator 224 can remain stationary. As a result, when the closure grip 222 is adjacent to the stationary grip 220, as in FIG. 2C, the firing actuator 224 can extend out of the recess of the closure grip 222 and be in the accessible position. A user can move the firing actuator 224 toward the closure grip 222 to advance the cutting member (not shown) toward the jaws to cut tissue disposed therebetween, apply RF energy to the tissue, and/or apply staples or clips to the tissue. After a user has actuated the firing actuator 224, the firing actuator 224 can be locked inside of the recess in the closure grip 222 in the inaccessible position and the closure grip 222 can automatically move away from the stationary grip 220. This can also cause the jaws to open to release the tissue until the device 200 is in the initial position of FIG. 2A. A person skilled in the art will appreciate that the closing, firing, and releasing steps can be repeated any number of times.

The devices of FIGS. 3-6 can be used to cut tissue in similar ways. While reference is made to the reference numerals in FIG. 3, a person skilled in the art will appreciate that the surgical procedure can be performed using any of the other devices herein. In use, the surgical device 300 can be inserted in a patient in a second, closed position with jaws 316a, 316b of the end effector 314 closed and the closure grip 322 positioned substantially adjacent to the stationary grip 320 so as to minimize a size profile of the device 300 during insertion. When the end effector 314 is positioned in a patient's body, a user can apply a spreading force to the finger holes 322p, 320p of the closure grip 322 and of the stationary grip 320 to move the closure grip away 322 from the stationary grip 320, opening the first and second jaws 316a, 316b. With the jaws 316a, 316b so positioned, the firing actuator 324 of the device 300 can be inaccessible to a user to prevent a user from prematurely actuating it. When the first and second jaws 316a, 316b are positioned adjacent to tissue to be treated, a user can apply an inwardly directed force to the finger holes 320p, 322p of the closure grip 322 and of the stationary grip 320 to cause the jaws 316a, 316b to close and grasp the tissue therebetween. As this force is applied, the blocking arm 328 or blocking shield 428, 528 in FIGS. 3-5 can pivot or slide relative to the jaws 316a, 316b to begin exposing a firing actuator to a user. When the closure grip 322 is substantially adjacent to the stationary grip 320 and the jaws 316a, 316b of the end effector 314 are closed, the firing actuator 324 can be in an accessible position with the blocking shields/arms no longer obstructing a user's access to the firing actuator 324. A user can move the ring-shaped opening 334 and the slider 332 proximally to actuate a cutting member (not shown) and advance the cutting member toward the jaws 316a, 316b to cut tissue disposed therebetween, apply RF energy to the tissue, and/or apply staples or clips to the tissue. After a user has actuated the firing actuator, the closure grip can automatically move away from the stationary grip. This can cause the jaws to open and release the tissue. Additionally, the blocking arms/shields can automatically move into their initial position in which the firing actuator is inaccessible to a user. A person skilled in the art will appreciate that the closing, firing, and releasing steps can be repeated any number of times.

The device 600 of FIGS. 6A and 6B can be used to perform a surgical procedure in similar ways. When the device 600 is in the open position as in FIG. 6A, an inwardly directed force is applied to the device 600, the closure grip 622 can contact the protrusion 662 and exert a force on the firing actuator 624 that is greater than the biasing force applied by the torsion spring 666, causing the pivotable arm 660 and the ring-shaped member 634 to move toward the recess 668 of the stationary grip 620. When the closure grip 622 is substantially adjacent to the stationary grip 620 and the jaws 616a, 616b are closed, the firing actuator 624 can be in an accessible position with the ring-shaped member 634 disposed in the recess 668. A user can pull the ring-shaped member 634 proximally to advance a cutting member (not shown) toward the jaws 616a, 616b and cut tissue disposed therebetween, apply RF energy to the tissue, and/or apply staples or clips to the tissue. After a user has actuated the firing actuator 624, the closure grip 622 can automatically move away from the stationary grip 620. This can cause the jaws 616a, 616b to open and release the tissue. Additionally, the torsion spring 666 can move the ring-shaped member 634 to its initial position in which it is pivoted away from the stationary grip 620 and inaccessible to a user. A person skilled in the art will appreciate that the closing, firing, and releasing steps can be repeated any number of times.

The device of FIG. 7 can be used to cut tissue in a substantially similar way. When the device 700 is in the open position as in FIG. 7, as the inwardly directed force is applied to move the closure grip 722 toward the stationary grip 720, the mating feature 782 on the trigger 776 can directly contact the mating recess 784 formed on the slider 732. As the closure grip 722 moves toward the stationary grip 720, the base plate 772 can move in the same direction as the closure grip 722 and this can begin to expose the trigger 776 to a user. When the closure grip 722 is positioned adjacent to the stationary grip 720, the first portion 778 of the trigger 776 can be in the accessible position. The user can grasp the first portion 778 with one or more fingers and can pivot it proximally about the pivot point 774, thereby moving the slider 732 and the cutting member 730 distally toward the jaws 716a, 716b to cut tissue disposed between the jaws, apply RF energy to the tissue, and/or apply staples or clips to the tissue. After a user has actuated the firing trigger 776, the closure grip 722 can automatically move away from the stationary grip 720. This can cause the jaws 716a, 716b to open and release the tissue. This can also cause the base plate 772 and the firing trigger 776 of the firing actuator 724 to move to the position shown in FIG. 7 in which the firing trigger 776 is inaccessible to a user. A person skilled in the art will appreciate that the closing, firing, and releasing steps can be repeated any number of times.

Any of the above-mentioned surgical methods can include applying energy, such as RF energy, to tissue grasped by the jaws either prior to, during, or after cutting of the tissue. In certain aspects, the devices can be operated to "cold-cut" the tissue and need not apply energy to the tissue.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   an end effector having first and second jaws configured to move relative to one another between an open position in which the first and second jaws are spaced a distance apart from one another and a closed position in which the first and second jaws are configured to grasp tissue therebetween; and
   a handle portion having
     a first actuator operatively associated with the first and second jaws and movable between a first position and a second position, movement of the first actuator from the first position to the second position being effective to move the first and second jaws from the open position to the closed position, and
     a second actuator configured to advance a cutting element distally along the first and second jaws to cut the tissue grasped therebetween, the second actuator having an opening configured to receive a user's finger; and
   at least one blocking member configured to move relative to the second actuator, movement of the first actuator from the first position to the second position being effective to move the at least one blocking member from an obstruction position in which the at least one blocking member obstructs the opening of the second actuator so that a user is hindered from actuating the second actuator, to a firing position in which the at least one blocking member is displaced away from the opening of the second actuator.

2. The surgical device of claim 1, wherein the at least one blocking member comprises first and second blocking members, the first blocking member configured to be positioned on a first side of the second actuator and the second blocking member configured to be positioned on a second side of the second actuator.

3. The surgical device of claim 1, wherein the at least one blocking member comprises a blocking shield configured to substantially cover the opening of the second actuator.

4. The surgical device of claim 1, wherein the at least one blocking member comprises a blocking arm configured to partially cover the opening of the second actuator.

5. The surgical device of claim 1, wherein the opening of the second actuator is configured to be exposed, in response to movement of the first actuator from the first position to the second position, such that the second actuator can be actuated to advance the cutting element.

6. The surgical device of claim 1, wherein the second actuator is configured to deliver energy to the tissue engaged between the first and second jaws as the cutting element is advanced distally along the first and second jaws.

7. A surgical device configured to grasp and cut tissue, comprising:
   an end effector including first and second jaws configured to move relative to one another between an open position in which the first and second jaws are spaced apart and a closed position in which the first and second jaws are configured to engage the tissue therebetween; and
   a handle assembly coupled to the end effector with the end effector being located distal of the handle assembly, the handle assembly having:
     a closure actuator configured to move the jaws between the open and closed positions,
     a firing actuator configured to advance a cutting member distally along the jaws to cut tissue engaged between the first and second jaws, and
     a blocking member configured to extend longitudinally across a finger recess of the firing actuator from a distal end of the finger recess to a proximal end of the finger recess when the first and second jaws are in the open position to thereby hinder a user from accessing the firing actuator, the distal end of the finger recess being more proximate to the end effector than the proximal end of the finger recess.

8. The surgical device of claim 7, wherein the blocking member is configured to move away from the finger recess when the first and second jaws are moved to the closed position.

9. The surgical device of claim 7, wherein the closure actuator comprises a first handle member of the handle assembly, and the firing actuator is mounted on a second handle member of the handle assembly, the first and second handle members being pivotally coupled to one another.

10. The surgical device of claim 9, wherein the blocking member is pivotally mounted on the second handle member.

11. The surgical device of claim 9, wherein the blocking member is linearly slidably mounted on the second handle member.

12. The surgical device of claim 11, further comprising a linkage member coupled between the blocking member and the first actuator, the linkage member being configured to exert a distally directed force on the blocking member when the closure actuator is actuated to move the first and second jaws from the open position to the closed position.

13. The surgical device of claim 12, further comprising a linkage member coupled between the closure actuator and the blocking member, the linkage member being configured to move the blocking member away from the finger recess when the first and second jaws are moved to the closed position.

14. A method for actuating a surgical device, comprising:
moving a closure actuator on a surgical device from a first position to a second position to cause first and second jaws of the surgical device to move from an open configuration in which the first and second jaws are spaced apart to a closed configuration in which the first and second jaws grasp tissue therebetween, wherein moving the closure actuator from the first position to the second position moves a blocking member from a first position, in which the blocking member extends across a finger recess of a firing actuator such that the finger recess is inaccessible to a user, to a second position, in which the blocking member is moved away from the finger recess such that the firing actuator is accessible to the user; and
with the first and second jaws in the closed position, moving the firing actuator on the surgical device to advance a cutting assembly along the first and second jaws to thereby cut the tissue grasped therebetween.

15. The method of claim 14, wherein the blocking member pivots from the first position to the second position.

16. The method of claim 14, wherein the blocking member slides longitudinally from the first position to the second position.

17. The method of claim 14, further comprising applying REF energy to the tissue grasped between the first and second jaws.

* * * * *